United States Patent
Zur (10) Patent No.: US 10,463,526 B1
(45) Date of Patent: Nov. 5, 2019

(54) PROGRAMMABLE PRESSURE MANAGEMENT SUPPORT SURFACE

(71) Applicant: Levy Zur, Boynton Beach, FL (US)

(72) Inventor: Levy Zur, Boynton Beach, FL (US)

(*) Notice: Subject to any disclaimer, the term of this patent is extended or adjusted under 35 U.S.C. 154(b) by 0 days.

(21) Appl. No.: 15/973,418

(22) Filed: May 7, 2018

(51) Int. Cl.
- *A61F 5/32* (2006.01)
- *A61H 9/00* (2006.01)
- *A61F 5/34* (2006.01)
- *A61M 39/22* (2006.01)

(52) U.S. Cl.
CPC ............ *A61F 5/32* (2013.01); *A61F 5/34* (2013.01); *A61H 9/0078* (2013.01); *A61M 39/223* (2013.01); *A61H 2201/501* (2013.01); *A61M 2205/3344* (2013.01); *A61M 2205/50* (2013.01)

(58) Field of Classification Search
CPC ........... A61F 5/34; A61F 5/35; A61H 9/0078; A61M 39/223
See application file for complete search history.

(56) References Cited

U.S. PATENT DOCUMENTS

| | | | |
|---|---|---|---|
| 4,542,547 A | 9/1985 | Sato | |
| 5,003,654 A | 4/1991 | Vrzalik | |
| 5,375,273 A | 12/1994 | Bodine, Jr. et al. | |
| 5,611,096 A | 3/1997 | Bartlett et al. | |
| 5,873,137 A | 2/1999 | Yavets-Chen | |
| 6,119,291 A | 9/2000 | Osborne et al. | |
| 6,560,803 B2 * | 5/2003 | Zur | A61G 5/1043 297/284.6 |
| 6,584,628 B1 | 7/2003 | Kummer et al. | |
| 6,623,080 B2 | 9/2003 | Clapper | |
| 6,877,178 B2 | 4/2005 | Chapman et al. | |
| 6,892,405 B1 | 5/2005 | Dimitriu et al. | |
| 6,910,238 B2 | 6/2005 | Biggie et al. | |
| 7,156,467 B2 | 1/2007 | Kimmig | |
| 7,219,380 B2 | 5/2007 | Beck et al. | |
| 7,278,179 B2 | 10/2007 | Schneider | |
| 7,409,735 B2 | 8/2008 | Kramer et al. | |
| 7,469,436 B2 | 12/2008 | Meyer et al. | |
| 7,657,956 B2 | 2/2010 | Stacy et al. | |
| 7,849,545 B2 | 12/2010 | Flocard et al. | |
| 7,877,829 B2 | 2/2011 | Gonzalez et al. | |
| 8,011,045 B2 | 9/2011 | Skripps | |
| 8,052,630 B2 | 11/2011 | Kloecker et al. | |
| 8,413,271 B2 | 4/2013 | Blanchard et al. | |
| 8,776,290 B2 | 7/2014 | Wilkinson et al. | |
| 8,863,336 B2 * | 10/2014 | Theosabrata | A47C 19/025 5/652.1 |

(Continued)

*Primary Examiner* — Timothy A Stanis
(74) *Attorney, Agent, or Firm* — The Keys Law Firm, PLLC (57) ABSTRACT

A support surface having a plurality of small, independent, cylinder shape, vertically mounted air cells integrated on a hospital bed, nursing home or home care beds or as a mattress replacement. The pneumatic support surface is electronically controlled and operated by a caregiver through the only external part of the system: a smartphone or a tablet. The support surface is capable to perform separately or in succession, within two hours, several cycles of a plurality of known procedures for the prevention of pressure sores plus a unique procedure focused on the most-risky parts of the body combined with a program that provides optimum conditions for best and faster healing of existing pressure injuries.

14 Claims, 9 Drawing Sheets

(56) References Cited

U.S. PATENT DOCUMENTS

| | | | |
|---|---|---|---|
| 8,973,193 B2 * | 3/2015 | Codos | A47C 27/10 5/706 |
| 9,015,885 B2 * | 4/2015 | Chapin | A47C 27/10 5/710 |
| 9,591,995 B2 * | 3/2017 | Blumberg | A47C 23/002 |
| 2002/0013967 A1 | 2/2002 | Roux | |
| 2004/0103478 A1 | 6/2004 | Ellis et al. | |
| 2004/0226103 A1 | 11/2004 | Reger et al. | |
| 2005/0081300 A1 | 4/2005 | O'Reagan et al. | |
| 2006/0016016 A1 | 1/2006 | Hornbach | |
| 2006/0026767 A1 | 2/2006 | Chambers et al. | |
| 2006/0085919 A1 | 4/2006 | Kramer et al. | |
| 2006/0117482 A1 | 6/2006 | Branson | |
| 2006/0236464 A1 | 10/2006 | Beck et al. | |
| 2008/0052837 A1 | 3/2008 | Blumberg | |
| 2010/0205750 A1 | 8/2010 | McCausland et al. | |
| 2010/0308846 A1 | 12/2010 | Camus | |
| 2011/0263950 A1 | 10/2011 | Larson et al. | |
| 2012/0061943 A1 | 3/2012 | Nihei | |
| 2013/0019408 A1 | 1/2013 | Jacofsky et al. | |
| 2013/0255699 A1 | 10/2013 | Squitieri | |
| 2014/0310881 A1 | 10/2014 | Wyatt et al. | |
| 2014/0352074 A1 * | 12/2014 | Stacy | A61G 7/015 5/713 |
| 2015/0094618 A1 | 4/2015 | Russell et al. | |
| 2016/0008196 A1 | 1/2016 | Britton | |

\* cited by examiner

PROGRAMMABLE PRESSURE MANAGEMENT SUPPORT SURFACE

BACKGROUND OF THE INVENTION

The present disclosure relates to support surfaces for homecare, acute care and long-term care facilities and, in particular, a mattress replacement support surface capable to perform multiple protocols for the prevention and the treatment of pressure injuries and other medical complications.

Pressure applied to the skin against bony parts of the body disrupts the blood circulation through the capillaries, causes a decreased supply of oxygen and nutrition to the tissue and, if prolonged, may cause the development of pressure sores. Pressure and the duration of pressure have an inverse relationship. The NPUAP (National Pressure Ulcer Advisory Panel) defines a pressure ulcer as an area of unrelieved pressure over a defined area, usually over a bony prominence, resulting in ischemia, cell death, and tissue necrosis.

The average capillary blood flow pressure on healthy people is believed to be 32 mmHg. However, it is well documented that different anatomical locations have a large verity of pressure in their capillaries with values reduced for the elderly and by sickness. When external pressure is higher, blood flow is obstructed and circulation reduced or stopped, setting the stage for pressure sore to form.

In healthy, alert people, the discomfort produced by local pressure that might cause interruption of the blood flow, even as small as a wrinkle in a bed sheet, is normally severe enough to cause a small movement to relieve the pain. But if a person cannot sense or respond to the pain, the ischemia may be prolonged sufficiently to cause cell death resulting in a pressure sore.

Pressure sores do not originate in the skin but rather in the deep tissues where the pressures, due to internal bony prominences, are higher than on the skin itself. Also, muscle tissue is more sensitive than skin to pressure-induced ischemia and while the skin may be just discolored, the muscle underneath may be already necrotic.

Although there are other contributing factors such as sheer, friction, moisture, dryness of the skin resulting from poor nutrition, the most important factor in the development of pressure ulcers is unrelieved pressure. The level of pressure and the duration necessary to cause an ulcer have an inverse relationship. Therefore, the real solution rests in dealing with both parts of the equation: pressure and time.

The most common, but not exclusive sites of occurrence of pressure ulcers include the ischium (28%), the sacrum (17-27%), the trochanter (12-19%), and the heel (9-18%).

Individuals with mobility impairments that prevent independent repositioning are at high risk for developing pressure sores. It mostly affects the frail elderly and the immobile severe physically disabled, and costs the national budget billions of dollars each year. The NPUAP ranks four stages of pressure injuries, the lowest being "non-blanchable erythema" and the highest being "full-thickness skin and tissue loss", with additional "unstageable pressure injuries" beyond this.

Support surfaces are classified by Medicare in three categories: Class 1 for passive support surfaces such as foam, gel, air mattresses; Class 2 for powered or active mattresses replacement and Class 3 for air-fluidized beds.

There are three basic methods utilized for prevention of pressure sores. One method is pressure redistribution (often confused with the term "low-air-loss" which according to NPUAP's definition is a feature of support surfaces that provides a flow of air to assist in managing the microclimate of the skin) where the purpose is to minimizing the risk for formation of pressure injuries by widely spreading the weight of the body over the support surface and reducing the pressure at the site of the bony parts of the body. Passive mattresses of foam, gel, water or air, some Class 2 powered support surfaces and Class 3 Air Fluidized bed strive to redistribute the pressure and reduce it from the risky parts of the body.

Another method utilized for prevention of pressure sores is alternating pressure. Support surfaces that perform this method are powered systems categorized by Medicare as Class 2. Typically, these support systems consist of a number of lateral, tubular air compartments, interconnected in two groups. One group having the even compartments interconnected, the other group having the odd compartments interconnected. When one group inflates, the other deflates. Some companies converted the tubular compartments to air cells of different shapes, but the principal of operation persisted: half of the cells inflate while the other half deflate. Although very popular, this method's efficacy is questionable since practically it reduces the area supporting the body to 50% or, as many manufacturers do, not deflating the part supposed to deflate to under the capillary pressure.

Another method utilized for prevention is the lateral rotation. There are not many beds in the marketplace that perform lateral rotation. In this method the body is rotated sidewise, thus moving the points of contact between the body and the support surface to new locations. The lack of automated systems performing lateral rotation is replaced in acute and long-term settings with strong recommendation to manually turn patients sidewise at least every two hours.

The most sophisticated systems for the prevention and treatment of pressure sores are Air Fluidized beds classified by Medicare as Group 3. These beds provide better immersion than most other pressure redistribution support surfaces in the market but are very heavy, noisy, expensive and inappropriate to perform CPR if cardiac arrest occurs. Air Fluidized beds are based on technology 40-50 years old.

There are numerous studies comparing systems representing one or other of these methods for prevention of pressure injuries to a standard hospital bed. There are, however, a limited amount of good, reliable studies comparing one of these methods to another. Most studies conclude that no evidence suggests that one method performs better than the others. There are not guidelines telling caregivers when or in what cases to use one method or the other and so patients are provided with whatever is available or cheaper, regardless efficacy.

Attempts have been made to combine the functionality of multiple systems. While many support surfaces claim to feature multiple functionalities, in most cases, these products perform one of the above described methods of prevention (discussed in greater detail below) combined with a low-air-loss method. Low-air-loss is a term introduced decades ago by a company that was praising the cover of its mattress relative to the quality of their competitors. A second conglomerate responded by punching holes in the air tubes and called it "the true low-air-loss". The NPUAP responded in a set of meetings of the best clinicians in the nation stated that low-air-loss is not a method for prevention of pressure injuries but rather "a feature to assist in managing the microclimate of the skin.

As such, a problem that still exists is that no existing support surface is capable of performing each one of the three preventive methods (pressure redistribution, alternating pressure, lateral rotation) separately or in combinations chosen by the clinician. An additional problem which still exists is that no existing support surface is capable of performing an intense preventive procedure at several high-risk locations while the remaining of the support surface continues its ordinary preventive methods of operation. And yet another additional problem which still exists is that no existing support surface is capable of performing all three preventive methods in a combination chosen by the clinician while at the same time reducing the interface pressure in several locations in the support surface to lower than capillary pressure thus providing optimum conditions for better and faster healing of existing injuries.

To improve the efficacy of support surfaces, many companies provide pressure mapping using measurements taken intermittently by external systems such as Tekscan® and Xsensor®. None has a continuous, integral, displayed and recorded interface pressure measurement system of its own.

SUMMARY OF THE INVENTION

The present disclosure describes a pneumatic, computer controlled programmable pressure management support surface capable of perform each one of the three standard methods for the prevention of pressure ulcers along with a fourth protocol unique to the present disclosure and a fifth specific protocol to assist in a better and speedier healing of existing pressure sores.

Accordingly, a multiple program pressure management support surface for the prevention and treatment of pressure injuries includes an elongated base having a top portion and a planar bottom portion and constructed of a rigid material, with the top portion including a pair of elevated longitudinal edges, on opposing sides of the base; a plurality of discrete, identical or variable, inflatable air cells mounted to the top portion between the longitudinal edges, each positioned over a hole in the top portion and oriented to extend vertically beyond the elevation of the longitudinal edges; a layer of foam on the elevated parts of the base, positioned to create a level top surface with the plurality of air cells when the plurality of air cells are inflated; an air supply system which includes a plurality of multi channel valves, at least one compressor, and main supply tubing which connects the at least one compressor with the plurality of multi channel valves so as to allow air output from the at least one compressor to be directed to each of the plurality of multi channel valves; and a control system having an internal controller and a plurality of row controllers and configured to supply power to at least the internal controller and the plurality of row controllers from an internal power supply, wherein said each of said plurality of row controllers is operatively connected to one of the plurality of multi channel valves so as to selectively permit and restrict the flow of air to and from the air cells, by individual air cell.

It is an object of the invention described herein to provide a programmable pressure management support surface capable of performing each one of the three preventive methods (pressure redistribution, alternating pressure, lateral rotation) separately or in combinations chosen by the clinician.

It is another object of the invention described herein to provide a programmable pressure management support surface capable of performing an intense preventive action at several high-risk locations while the remaining of the support surface continues its ordinary preventive methods of operation on the remaining of the body.

It is yet another object of the invention described herein to provide a programmable pressure management support surface capable of performing all three preventive methods in a combination chosen by the clinician while at the same time reducing the interface pressure in several locations in the support surface to lower than the capillary pressure and provide optimum conditions for better and faster healing of existing injuries.

It is still another object of the invention described herein to provide for mapping of interface pressure on the programmable pressure management support surface that automatically measures, displays and records the interface pressure continuously.

Structurally, the support surface described herein advantageously provides for all electronic and pneumatic components taking part in operating the system to be inserted within the two elevated sections of the base of the support system, with the sole except of the external controller which might be a smartphone or other computer device used by the operator.

Moreover, the support surface described herein advantageously provides independent segments of four, five or six rows allows, under certain circumstances, to combine very efficient prevention or treatment where needed with very low cost segments of foam where no risk or very low risk exists.

These and other objects and advantages will be apparent to one of skill in the art.

DETAILED DESCRIPTION OF THE INVENTION

Applicant's support surface described herein provides a full support system to be used as a mattress replacement or as an integral part of a bed that is capable of performing the various methods for the prevention of pressure sores, separately or in sequence, while also creating optimal conditions for better and faster healing of existing pressure injuries.

Figure 1:
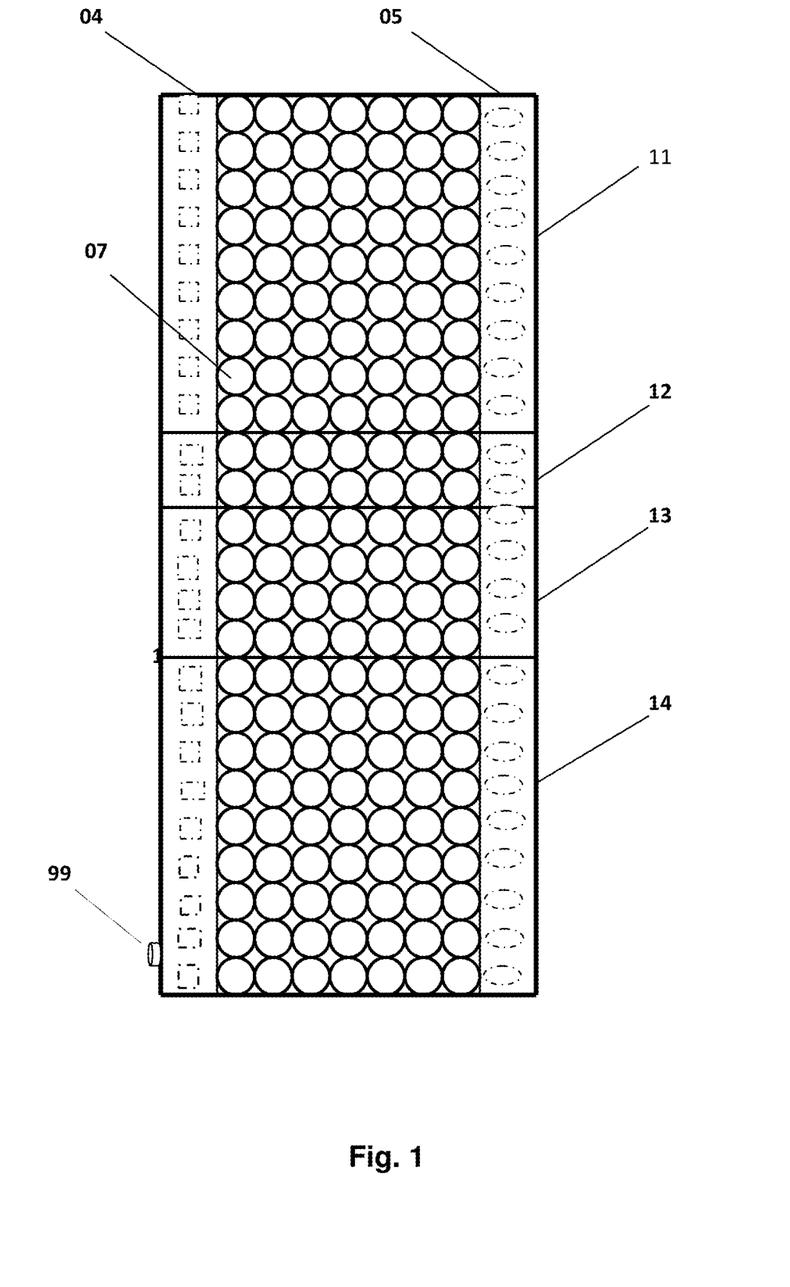
FIG. 1 is a top plan schematic view of a programmable pressure management support surface built in accordance with an embodiment of the present disclosure.
Figure 2:
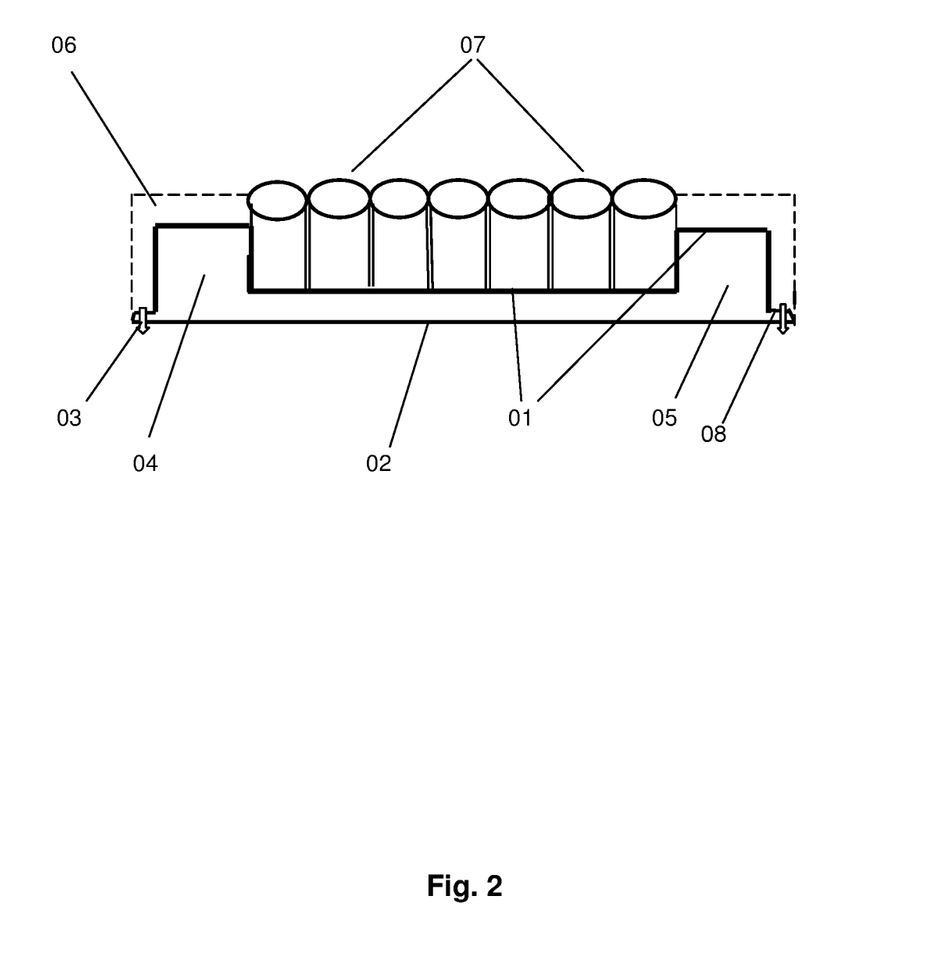
FIG. 2 is a partial front perspective view of one of the rows of a programmable pressure management support surface built in accordance with an embodiment of the present disclosure.
Figure 4:
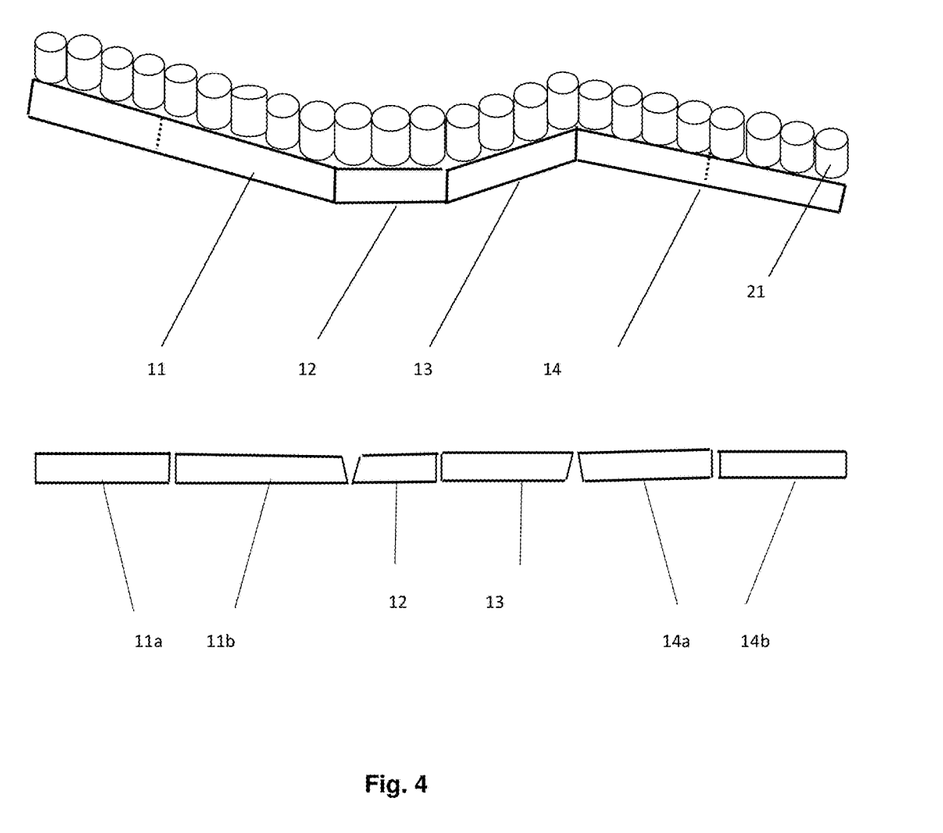
FIG. 4 is a partial side perspective view of one column of air cells of a programmable pressure management support surface built in accordance with an embodiment of the present disclosure placed on four segments of a Fowler hospital bed.

Referring now to the drawings and, in particular, to FIGS. 1, 2, and 4, a programmable pressure management support surface in accordance with the present disclosure is shown having a base, twenty-four (24) rows of seven (7) air cells 07, two longitudinal edges 04, 05 which define elevated areas on opposing sides of the base of the support surface, and a CPR push button 99. The support surface may include a plurality of segments 11, 12, 13, 14 which are sized to correspond to the segments of a Fowler hospital bed.

As illustrated in FIG. 2, the base of the support surface is formed from an upper layer 01 and a bottom layer 02. The upper layer 01 and bottom layer 02 may be fastened with screws 03 or other elongated fasteners passing through a ledge 08 on the upper layer 01 into the bottom layer 02. The upper layer 01 includes a low elevation running longitudinally between the longitudinal edges 04, 05. The plurality of rows of inflatable air cells 07 are disposed in the low elevation, vertically mounted on the upper layer 01 and standing upright. Advantageously, the elevated longitudinal edges 04, 05 serve as a rigid containment border which operates to maintain the inflatable air cells 07 in close proximity to each other at all times and prevent any lateral expansion beyond the profile of the low elevation.

The longitudinal edges 04, 05 is shown covered by a layer of foam 06 so as provide a surface on either side of the inflated cells 07 that rises vertically to a level that is substantially equal to that of the inflated cells 07 when fully inflated.

The upper layer 01 of the base of the system shown in FIG. 2 is a vacuum formed layer using acrylonitrile butadiene styrene ("ABS") or similar material. The bottom layer 02 of the base may be an integral part of a bed or a separate hard base forming a mattress replacement.

In the case of a mattress replacement, the entire base might be built of several sections to conform to a standard home bed, a nursing home bed or, as shown in FIG. 1 and FIG. 4, a fowler hospital bed having a first segment 11 supporting the head and the upper body, a second segment 12 for the coccyx and the ischial tuberosities, a third segment 13 for the thighs, and a fourth segment 14 for the legs of the person lying on the support surface.

Referring now to FIGS. 1, 2, 3, 4, 5, and 6, the space between the upper layer 01 and bottom layer 02 created by elevations of the longitudinal edges 04, 05 is sized to accommodate all parts required for the operation of the system, including but not limited to:
 a. A multi-channel valve 33 and a row controller 47 in each of the 24 rows of air cells 07; and
 b. One or more mini air compressor 31, pressure sensor 38, minimizer solenoid valve 39; one or more rechargeable batteries 43; the main PCB 44 with the CPU 45 that communicates with the external control unit 46.

Referring to FIG. 4, it is contemplated that rows of air cells must be grouped to account for the segmentation of the support surface which enabled the support surface to be suitable for a typical fowler hospital bed. As FIG. 4 only shows a single column, it is appreciated that each cell corresponds the row of which the shown cell belongs. It is also contemplated, however, that the segmentation of the support surface might change depending on the type of bed to be used. For example, the upper portion of FIG. 4 shows the breakdown of one column of air cells placed on four segments of a Fowler hospital bed, while the lower portion shows the breakdown of the support surface with segment 11 and segment 14 each divided in two parts 11a, 11b and 14a, 14b, respectively, for ease of transportation and handling.

In an embodiment with twenty four (24) rows and seven (7) cells in a row, it is contemplated that a common and easy to handle apportionment for transportation and installation might be segments of four (4) rows of seven (7) air cells.

Figure 3:
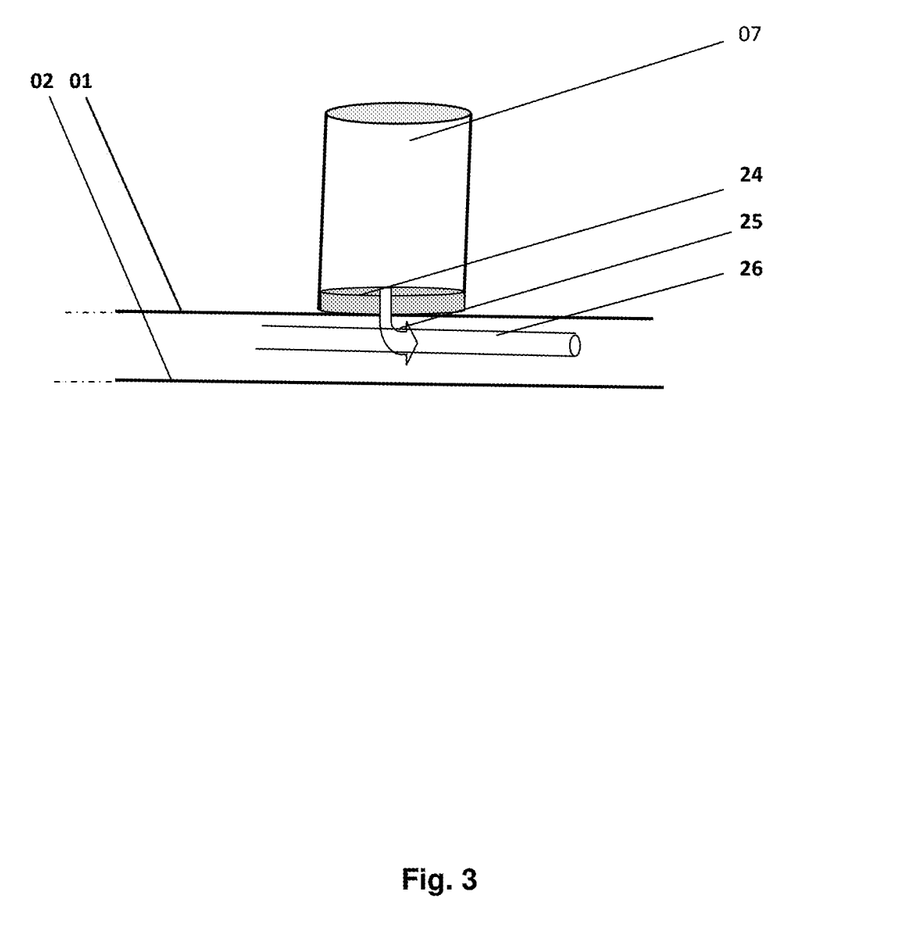
FIG. 3 is a partial elevational view of an air cell of a programmable pressure management support surface built in accordance with an embodiment of the present disclosure show with its connection to the air supply chain.
Figure 5:
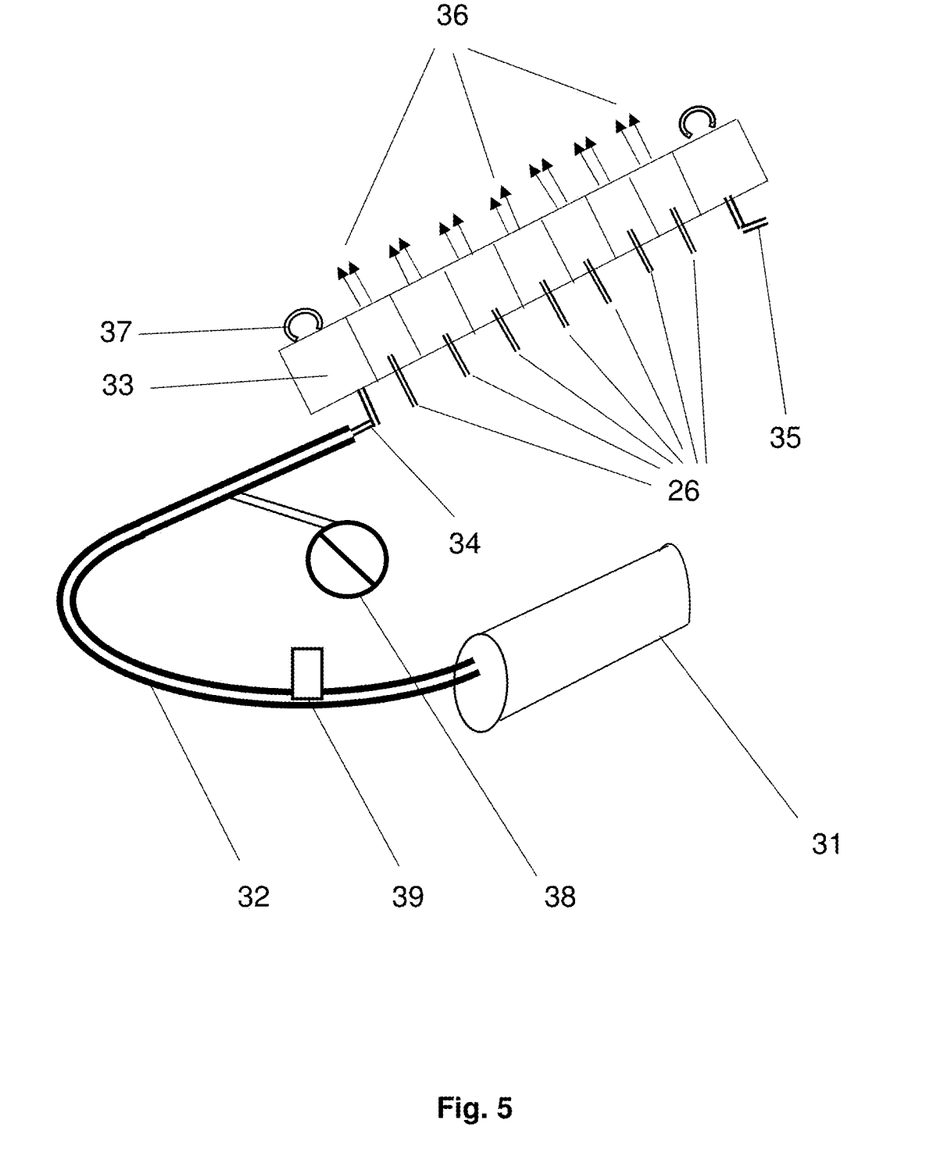
FIG. 5 is a schematic of an air supply system for a programmable pressure management support surface built in accordance with an embodiment of the present disclosure.

Referring to FIGS. 3 and 5, inflatable air cells 07 forming the support surface are produced from soft, non-stretchable air-tight fabric. These air cells 07 are each connected to an air supply chain. In embodiments of the support surface in which the air cells 07 are round, a ring 24 of ABS or similar material may be placed and sealed inside at the bottom of the cell 07. Each air cell 07 has an opening in the bottom in which a rubber or plastic fitting 25 is inserted and sealed to the fabric. The ring 24, with the fitting 25 being an integral part of it or attached thereto (by being, for example, screwed or glued together), prevent the cell 07 from ballooning when fully inflated. The fitting extends through a hole in the base 01 and connect to a flexible tube 26 that links to the multi-channel valve 33 as shown in FIG. 3 and FIG. 5. Through such a link, the tube 26 is operative to supply or release the pressurized air to or from the cell 07.

Figure 6:
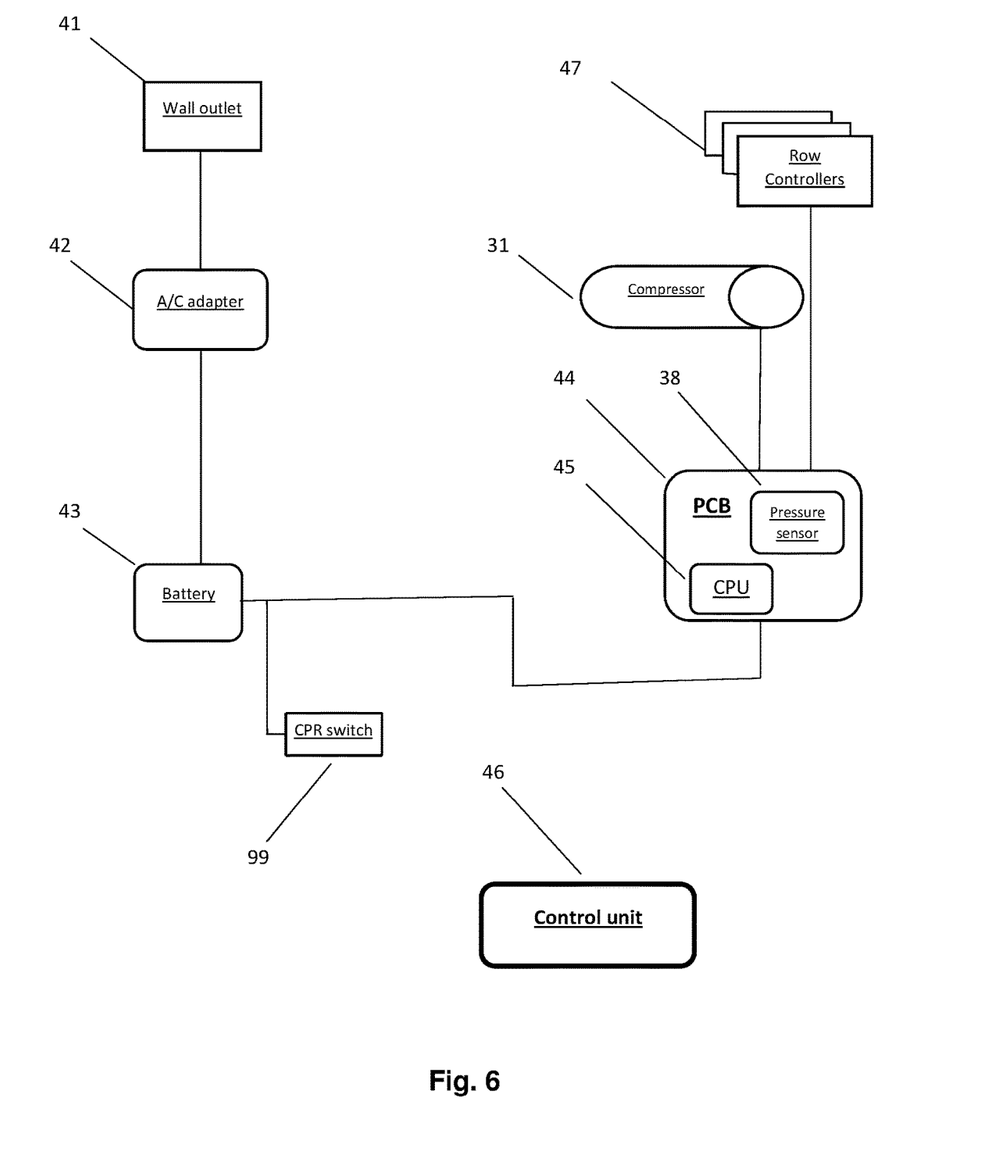
FIG. 6 is a block diagram showing the electrical and control systems of a programmable pressure management support surface built in accordance with an embodiment of the present disclosure.

Referring now to FIGS. 5 and 6, the air supply system includes an air compressor 31, main supply conduit tubing 32, a plurality of multi-channel valves 33, with the tubing 32 linking the compressor 31 and each respective multi-channel valve 33. Each multi-channel valve 33 connects selectively between the main supply conduit 32 and any combination of air cells 07 through tubes 26. Each channel connects to one air cell 07 in the row controller 47. Each multi-channel valve 33 has an entry of air 34 from the compressor 31 and an exit 35 of compressed air from the cell to the atmosphere. It also has two holes 37 for screws and bolts to fasten the multi-channel valve 33 to the base.

The compressor 31, multi-channel valve 33 and pressure sensor 38 may be off-the-shelf items.

Each multi-channel valve 33 is controlled by the CPU 45 through the row controller 47 which corresponds to the specific row for the given multi-channel valve 33. And each channel in the multi-channel valve 33 is connected to the row controller 47 by a pair of wires 36. Each row of air cells 07 may have its multi-channel valve 33 located in the space under the longitudinal edge 04, 05 on one side and the row controller 47 located in the space on the other side.

Each channel in the multi-channel valve 33 may be set to one of three states:
 open to receive air to the cell
 close and passive
 open to release air from the cell to the atmosphere When the compressor 31 pumps air and one of the seven channels in the multi-channel valve 33 connecting to one of the seven air cells 07 is open to receive air, the pressure measured by the pressure sensor 38 is the same in the supply conduit 32 and in the air cell 07. As such, by appropriate selection of the state of the pressure control system synchronized with the opening of the selected channel, the pressure in any air cell 07 may be measured and controllably increased or decreased.

The entire system may operate internally on 24V, supplied by rechargeable battery or set of batteries 43 that are charged from the wall outlet 41 through a medical grade A/C adaptor 42. The battery 43 energizes a PCB 44 that contains a CPU 45 with the software and the programming that includes the procedures performed in the present disclosure, a pressure sensor 38 with its circuitry, an interface with the compressor 31 and an interface with each of the twenty-four (24) row controllers 47 ("slaves"). The control unit 46, which preferable is a smart phone, but also might be other computer such as a tablet, laptop computer, or a nurse station full size desktop central computer, communicates with the CPU 45 located in the PCB 44 through a wireless serial interface, such as Bluetooth Low Energy (BLE).

The entire system may alternatively operate internally on 12V.

The CPR button (or panic button) 99, shown spatially in FIG. 1, cuts the supply of electricity to the system. At this instant all channels in all multi-channel valves 33 turn in to the closed position; no air goes in or out of the air cells. Thus, the dynamic support surface turns into a hard support surface allowing to performing CPR or any other medical emergency procedure instantly, without any delay.

The system is set in motion by an operator after choosing the programs suitable to the person treated and setting the adequate parameters on the remote control unit 46. The information is transmitted to the CPU 45. The CPU 45 communicates with each of the row controllers' 47 processors using two wire communication bus. The row controllers 47 are addressed by means of dipswitches installed on the row controllers 47. The addressed row controller 47 processor executes the command and returns a completion message to the CPU 45. The commands that the row controller 47 processor can execute are:

1. Open a single channel for a target cell;
2. Close a single channel for a target cell;
3. Open all channels in the row; and
4. Close all channels in the row.

Upon activating the system and establishing contact between the remote control unit 46 and the PCB 44, the screen of the remote control unit 46 would show a main menu to include:

Programs;
Parameters; and
Pressure Measurements.

The main menu on the remote control unit 46, on the PROGRAMS page, the display may show the list of procedures available as modes of operation for the operator to choose from:

Pressure Redistribution;
Alternating Pressure;
Lateral Rotation;
Rotating Pressure Relief;
Lasting Pressure Relief;
Combined Programs; and
Manual Operation.

Modes of Operation

Turning now to the specifics of the various modes of operation, the present disclosure teaches a full support system capable of performing multiple methods for the prevention of pressure injuries, separately or in sequence, while also creating optimal conditions for better healing of open wounds.

The software for the various programs operated by the present disclosure is written and stored in the CPU located on the main PCB.

Pressure Redistribution (P/R)

P/R is a preventive method that strives to alleviate the pressure on the bony parts of the body and attempts to equalize the interface pressure over the entire body positioned on the support surface.

In the P/R procedure, the pressure sensor measures the pressure in each air cell, one at a time, starting at row number one (1) at the top of the support surface, followed by next row until row number twenty four (24) and back to row number one (1). It analyzes the pressure measured in each cell and responds by micro-step changes in the inner pressure of the cells inflating the support surface to a predetermined level set by the clinician in consideration of the patient's weight and other factors.

After a few cycles of gradual inflation, the system will follow with a number of cycles of pressure measured deflation performed by fast screening of the pressure in each one of the air cells, detecting the high-pressure points and reducing the pressure by minuscule release of pressurized air from the cell. At the end of the pressure redistribution procedure the support surface would adjust to the contour of the body and the interface pressure would fall under the capillary pressure in any point of contact between the body and the support surface. The constant inflation/deflation of one cell at a time provides also a therapeutic massage effect on the body. After resting in this position for a few minutes, the cells will re-inflate and the procedure will repeat itself. One full cycle of P/R might last approximately 20 minutes.

The operator of the system may be able to regulate parameters of the P/R procedure through the screen of the remote control unit 46. These parameters may include, but not limited to:

Maximum pressure—indicating maximum inflatable pressure allowed for air cells; the figure might be in PSI or other features.
Inflation steps—number of inflation cycles to reach maximum press.
Inflation delta—the addition of pressure in each inflation cycle.
Deflation cycles—number of deflation cycles allowed.
Deflation time—duration of the deflation of each air cell.
Rest time—allowable time before re-inflating the support surface.
Inflation order—in the rows.
Deflation order—in the rows.

Alternating Pressure (a/P)

Although overloaded with flaws, the A/P method for the prevention of pressure sores is the most common powered support surface existing in the market place. The A/P method operates on the time element in the equation of pressure and time (discussed in greater detail above).

Unlike all other existing A/P support surfaces that inflate and deflate 50% of their compartments at once, the present support surface activates only one row at a time: it inflates row #1, deflates row #2, inflates row #3, deflates row #4 and so forth. When finished 24 rows, it deflates row #1, inflates row #2 and so forth. Thus, when the A/P mode is operated, the present support surface creates a wave that repetitively changes the point of touch between the body and the support surface and constantly massages the body. Furthermore, the system may be set for a double wave or more, thus increasing the impact of the A/P method and the massage effect on the body of the patient. A full cycle of a double A/P mode may take approximately 5 minutes.

The operator of the system may be able to regulate parameters of the A/P procedure through the screen of the control unit. These parameters may include, but not limited to:

Initial pressure—the maximum pressure to start the cycle of deflation.

Maximum pressure—higher than the initial pressure to avoid bottoming out.

Single/double wave.

Lateral Rotation (L/R)

L/R is a required procedure in all institutional settings to be performed every two hours. In most institutes it is done manually for lack of powered systems. Very few support systems exist in the market place that perform lateral rotation.

In the L/R mode the present disclosure's system operates much the same as in the P/R mode except that the pre-programmed screening of the air cells is in order of columns rather than rows. Thus, while in P/R mode the computer screens [row 1] air cells, then [row 2], [row 3], [row 4], etc., in the L/R mode the computer screens columns of air cells in a pre-programmed order so that one side of the support surface inflates while the other side deflates, gradually rotating the body to the side. When maximum rotation has been reached, the system would pause to maintain the body on the side position for a predetermined time. Then, the computer, through several cycles of screening, pressure measuring and analyzing, reduces the pressure in the cells of the inflated columns and increases the pressure in the opposite side, thus slowly rotating the body the other way. A full cycle rotation to both sides and back to neutral position may take approximately 40 minutes.

The L/R parameters are identical to the P/R parameters except that the inflation and deflation order requires more detailed specifications.

Rotating Pressure Relief (RPR)

The RPR method for the prevention of pressure sores is unique to the present disclosure. No other known support system in the market place is capable to perform a similar, highly efficient method of prevention. The RPR mode provides the ability to focus the preventative treatment to the riskier parts of the body like the coccyx, the ischial tuberosities, the heels, or to any other site that started to show signs of beginning developing a pressure injury. Depending on the number and the size of the areas treated, a typical cycle of RPR might take about 6 minutes.

Figure 7:
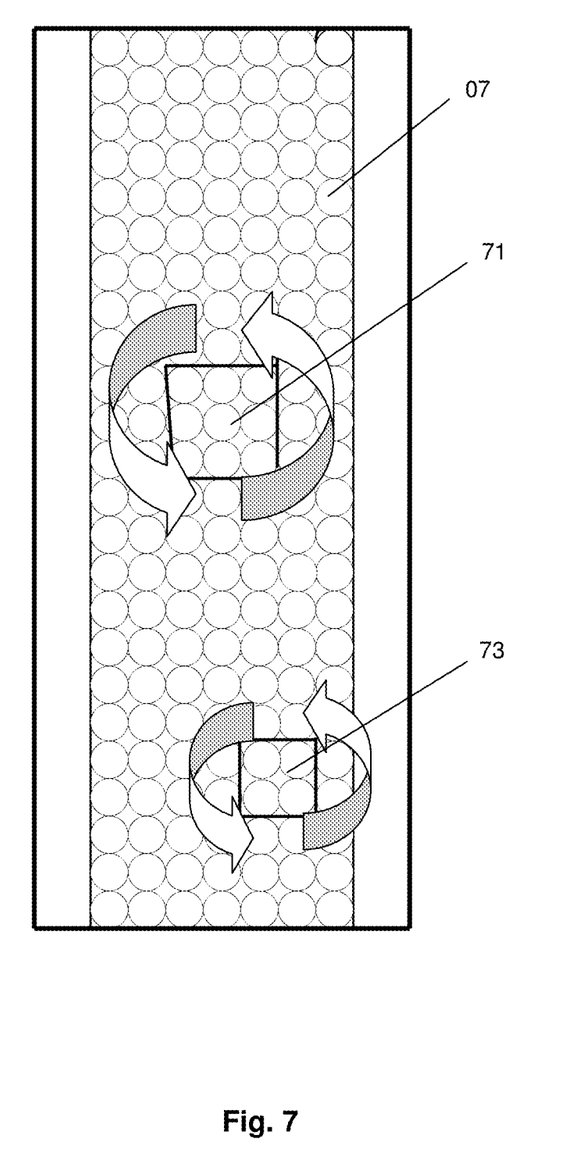
FIG. 7 is a schematic of a top plan view of a programmable pressure management support surface built in accordance with an embodiment of the present disclosure showing a typical Rotating Pressure Relief method at a corresponding location of a coccyx and a left heel of a user.

Referring now to FIG. 7, the RPR method may be applied to groups of air cells 07 in three locations on the support surface at the same time. The RPR method may alternatively be applied to more or less locations. FIG. 7 illustrates the RPR method applied to a first spot 71 and a second spot 73:

|  | Coccyx (71) | Left heel (73) |
| --- | --- | --- |
| Row | 10-12 | 20-21 |
| Column | 3-5 | 5-6 |

The operator of the system may be able to regulate parameters of the RPR procedure through the screen of the remote control unit device. These parameters may include, but not limited to:

The location of each spot treated;

The size of each spot treated; and

The duration of deflation.

Lasting Pressure Relief (LPR)

The LPR method of treatment in assisting for better and faster healing of existing pressure sores is unique to the present disclosure. The LPR mode of operation provides areas free of pulsating pressure and free of any pressure at all under the open wound so that the healing process may take its natural course without any external interference.

Figure 8:
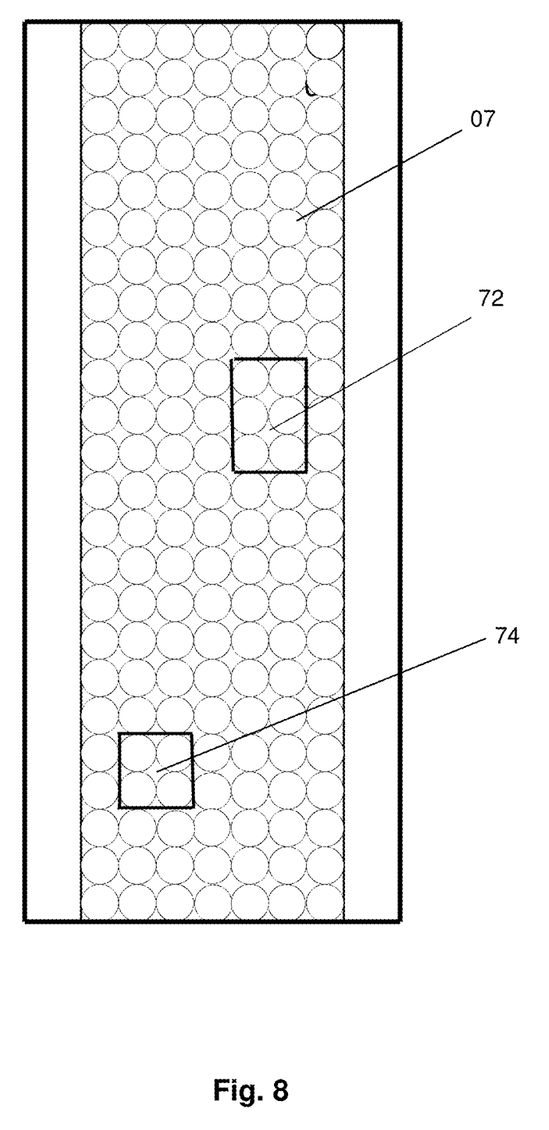
FIG. 8 is a schematic of a top plan view of a programmable pressure management support surface built in accordance with an embodiment of the present disclosure a typical Lasting Pressure Relief method applied at a corresponding location of a left IT and right heel.

Referring now to FIG. 8, the LPR method may be applied to three locations on the support surface at the same time. The LPR method may be applied to more or less locations at the same time. FIG. 8 illustrates the LPR method applied to a first spot 72 and a second spot 74:

|  | Left ischial tuberosity (72) | Right heel (74) |
| --- | --- | --- |
| Row | 10-12 | 20-21 |
| Column | 5-6 | 2-3 |

Combined Programs

Choosing COMBINED PROGRAMS mode, the operator of the system of the present support surface may be able to customize the treatment provided to a patient and deliver the best combination of methods of prevention along with assisting in the treatment and healing of existing pressure injuries.

As an example, during a period of two hours, an individual treated with the present support surface may receive:

2 cycles of P/R 2×20 for a total of 40 minutes 4 cycles of A/P 4×5 for a total of 20 minutes 1 cycle of L/R 1×40 for a total of 40 minutes 3 cycles of RPR 3×6 for a total of 18 minutes As stated in the previous paragraph, the clinician may prescribe any other combination of programs as he/she considers most suitable for the patient treated. As the treatment is in progress, the system allows to easily run changes in the program as considered proper.

Manual Operation

Manual Operation mode allows the operator to inflate or deflate an air cell, a row of cells or a column of cells. The operator also may specify the pressure limit.

Pressure Mapping

Back to screen of the main menu, as discussed above, when Pressure Measurements is chosen on the remote control unit, the display may show a chart with a grid of seven (7) columns and twenty-four (24) rows representing the support surface (or whatever the applicable number of rows and columns were for the support surface. The pressure applied by the body on each of the 168 air cells would illustrate, in numbers, shades or colors, presenting a mapping the pressure of the body on the support surface. If shades or colors is chosen, a small chart on the side would give a reading of the shades or the colors in mmHg. The pressure mapping data may be recorded on an (optional) erasable memory chip installed on the PCB and printed in pre-selected intervals.

Set the Support Surface in Motion

Upon selecting the mode of operation, the system is set in motion. The control unit sends a signal to the CPU indicating the program to be executed. Parameters are tested and compared against the defaults and a cycle of inflation starts followed by the procedure of deflation and inflation as directed by the relevant program stored with the software in the CPU.

Figure 9:
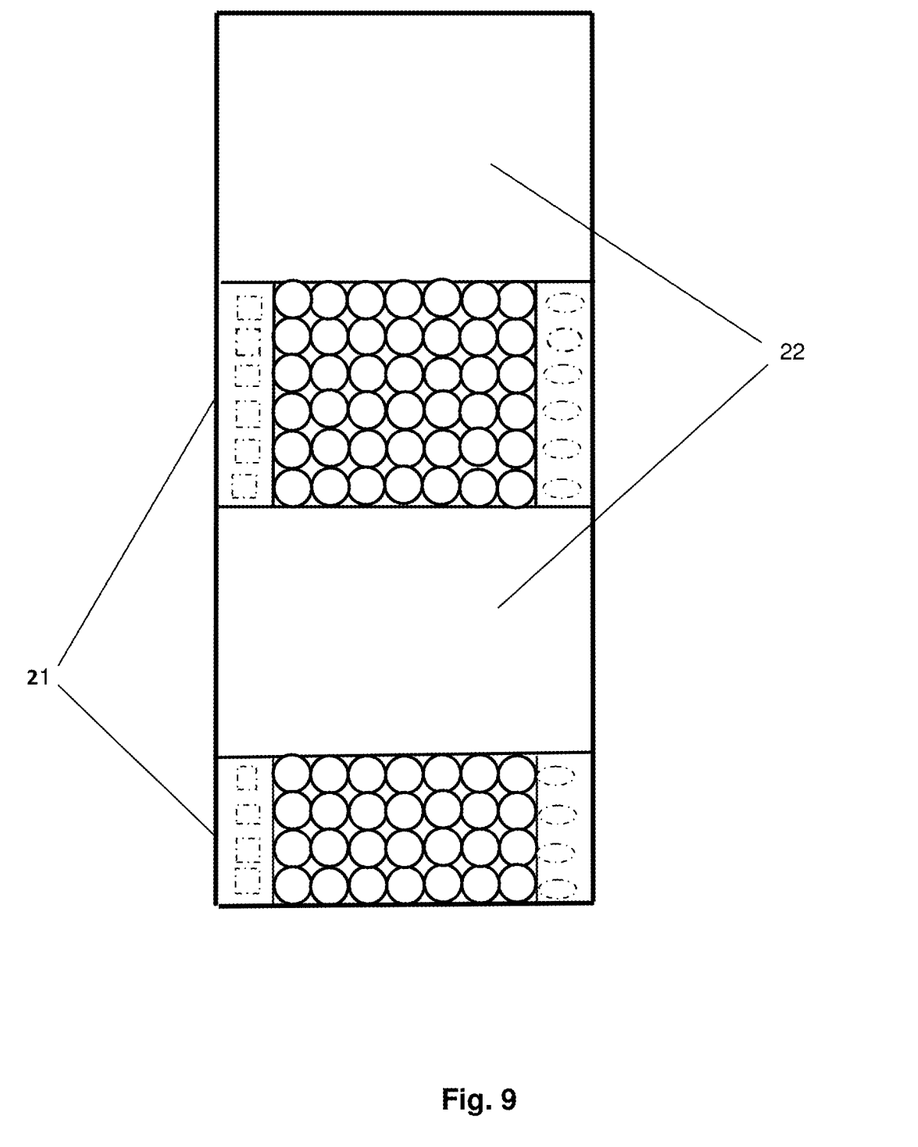
FIG. 9 is a schematic of a top plan view of a programmable pressure management support surface built in accordance with an embodiment of the present disclosure wherein operating segments having round air cells are located only under certain targeted locations.

Referring now to FIG. 9, in an alternate embodiment, a support surface may include therapeutic segments 21 formed from air cells similar to those described above only at well defined high-risk parts of the body. As illustrated, segments 21 of six (6) rows and four (4) rows with round cells would be placed at the high-risk locations of the individual laying on the support surface, while the rest of the support surface would be made up of relatively inexpensive foam segments 22.

It will be appreciated by those skilled in the art that the present disclosure may be useful for assisting in the treatment of additional medical complications such as:

INSOMNIA. The present support surface generates soothing massage cycles combined with gradual, very gentle yet complete immerse of the body into the support surface to the point that the pressure is equalized over the entire body. It maintains this position of complete immersion for as long as chosen by the operator then re-inflates the support surface applying various tender massage cycles and goes on and on for as long as required;

Assist in HEALING LOCALIZED BURNS using the LPR mode of operation thus avoiding contact between the support surface and the burned skin; and Assist in coping with BREATHING and LUNG PROBLEMS by increasing the massage effect of the support surface and increase use of the L/R mode of operation.

It is appreciated that the present disclosure advantageously provides an ability to perform separately each one of the basic three methods of prevention of pressure injuries, namely Pressure Redistribution, Alternating Pressure and Lateral Rotation, in preferred sequence and repetitive. In addition, real time customization enables user control of the parameters and sequence for each method before or during the operation of the system as well as the number of cycles for each.

It is appreciated that the present disclosure advantageously provides an ability to perform sequentially all three methods of prevention of pressure injuries, namely Pressure Redistribution, Alternating Pressure and Lateral Rotation, and have the treated individual benefit from the advantages of each one of these methods of prevention of pressure injuries formation It is further appreciated that the present disclosure advantageously provides an ability to incorporate a unique method of intensified preventive therapy, namely rotating pressure relief, in several locations identified at the individual treated as of very high risk for attaining high class pressure injury prevention.

It is further appreciated that the present disclosure advantageously provides an ability to incorporate such unique methods of assisting in better and faster healing of existing pressure injury by the ability to reduce for good the interface pressure at the location of one or more existing injury, thus avoiding cyclical pressure on the wound while healing.

It is further appreciated that the present disclosure advantageously provides a unique structure that allows all components participating in the operation of the support surface to be incorporated within the base of the mattress, with only the hand-held wireless discrete control unit of the system the only external part.

It is further appreciated that the present disclosure advantageously provides an ability to transfer the ever-changing position of the support surface instantly in to a hard surface for CPR or any other medical emergency treatment by pressing the CPR/panic button.

It is further appreciated that the present disclosure advantageously provides constant pressure mapping with the ability for the pressure readings to be recorded and printed at predetermined intervals.

It is further appreciated that the present disclosure advantageously provides an ability to combine segments of the very therapeutic portions of this support surface, namely the portions with air cells, with large portions of very inexpensive portions of support surface such as foam, to personalize treatment and reduce costs.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. A programmable pressure management support surface, comprising:
    an elongated base constructed of a rigid material and having a top portion which defines the entirety of an upper layer of the elongated base and a bottom portion which defines a bottom layer of the elongated base, wherein said top portion includes a pair of longitudinal edges and a low elevation area running longitudinally in between the longitudinal edges, with each longitudinal edge in the pair of longitudinal edges being defined by a discrete area that is elevated relative to the low elevation area;
    wherein the elongated base is formed of a plurality of transverse sections in order to conform to a Fowler hospital bed, with the low elevation area rigidly fixed to the longitudinal edge on either side for the entirety of each of the plurality of transverse sections;
    a plurality of discrete, inflatable air cells constructed of non-stretchable material, wherein each of said air cells is mounted to the top portion in the low elevation area and positioned in a matrix of a plurality of linear rows and a plurality of longitudinal columns;
    an air supply system which includes a plurality of multi channel valves, at least one compressor, and main supply tubing which connects the at least one compressor with the plurality of multi channel valves so as to allow fluid material output from the at least one compressor to be directed to each of the plurality of multi channel valves, wherein each of said plurality of multi channel valves include a plurality of discrete channels which are each associated with one of the plurality of air cells, thereby enabling each of said plurality of multi channel valves to selectively distribute fluid material received from said at least one compressor to the air cells associated with the channels of the respective multi channel valve, with each of said air cells only associated with one of the channels from one of the plurality of multi channel valves;
    a control system having an internal controller and a plurality of row controllers and configured to supply electrical power to at least the internal controller and the plurality of row controllers from an internal electrical power supply, wherein said each of said plurality of row controllers is operatively connected to one of the plurality of multi channel valves so as to selectively permit and restrict the flow of fluid material to and from the air cells associated with the channels of the respective multi channel valve by individual air cell and said internal controller is configured to control the operations of each row controller;
    wherein at least the internal electrical power supply, the control system, the plurality of multi channel valves, and the at least one compressor are contained in the base, positioned directly under one or both of the pair of longitudinal edges; and a discrete, external control unit configured to communicate electrical signals with said internal controller wirelessly, receive electrical signals related to pressure measurements for each of the plurality of air cells, and generate a visual output related to said pressure measurements on a user interface.

2. The programmable pressure management support surface of claim 1, wherein said control system is configured to initiate a performance of an alternating pressure procedure which includes simultaneously causing a decrease in pressure through the release of fluid material to all of the air cells among the plurality of air cells that are positioned in each linear row of the plurality of linear rows, with the air cells in only one of the linear rows of the plurality of linear rows only being caused to decrease in pressure at a time.

3. The programmable pressure management support surface of claim 2, wherein the alternating pressure procedure includes simultaneously causing an increase in the pressure through the addition of fluid material to all of the air cells among the plurality of air cells that are positioned in a first linear row while simultaneously causing a decrease in the pressure through the release of fluid material to all of the air cells among the plurality of air cells that are positioned in a second linear row that is immediately adjacent to the first linear row.

4. The programmable pressure management support surface of claim 1,
wherein said control system is configured to initiate the performance of a pressure redistribution procedure which includes measuring the pressure in each of the plurality of air cells individually and selectively causing a decrease of the pressure in at least one of the air cells in the plurality of air cells through the removal of fluid material so as to balance the measured pressure across all of the plurality of air cells.

5. The programmable pressure management support surface of claim 1, wherein said control system is configured to initiate the performance of a lateral rotation procedure which includes causing the pressure in all of the air cells among the plurality of air cells that are positioned in a first set of longitudinal columns of the plurality of longitudinal columns to be decreased relative to the pressure in all of the air cells among the plurality of air cells that are positioned in a second set of longitudinal columns of the plurality of longitudinal columns, wherein the first set of longitudinal columns and the second set of longitudinal columns are positioned on opposing sides of a longitudinal center line of the elongated base.

6. The programmable pressure management support surface of claim 1, wherein said control system is configured to initiate the performance of a rotating pressure relief procedure which includes selectively causing an increase or decrease of the pressure through the addition or removal of fluid material to at least one relief set of air cells that includes at least three contiguous air cells among the plurality of air cells spread across at least one of the plurality of linear rows and the plurality of longitudinal columns.

7. The programmable pressure management support surface of claim 1, additionally comprising a panic switch configured to immediately cause the flow of fluid material to and from all of the plurality of air cells to be restricted so as to instantly cause the programmable pressure management support surface to become a hard surface.

8. The programmable pressure management support surface of claim 1, wherein said air cells are oriented to extend vertically beyond the elevation of the pair of longitudinal edges when fully inflated.

9. The programmable pressure management support surface of claim 8, additionally comprising at least one layer of foam, wherein the at least one layer of foam is positioned to cover each of the pair of longitudinal edges and configured to form a planar top surface along with the plurality of air cells when the plurality of air cells are inflated.

10. The programmable pressure management support surface of claim 1, wherein said top portion additionally includes at least one transverse mattress segment defined by the absence of any of the plurality air cells, wherein said at least one transverse mattress is positioned adjacent to the plurality air cells.

11. The programmable pressure management support surface of claim 1, wherein:
said top portion is fastened directly to said bottom portion, forming an enclosed space that extends under both longitudinal edges and the low elevation area in between said top portion and said bottom portion; and
for each of the plurality of transverse sections, the enclosed space is continuous.

12. The programmable pressure management support surface of claim 1, wherein the top portion includes at least one ledge which corresponds to each longitudinal edge and extends outwardly beyond the longitudinal edge to which the at least one edge corresponds.

13. The programmable pressure management support surface of claim 1, wherein said visual output related to said pressure measurements includes a spatial representation of pressure measurements for each of the plurality of air cells.

14. The programmable pressure management support surface of claim 1, wherein said control system is configured to initiate the performance of a lasting pressure relief procedure which includes selectively causing a decrease of the pressure through the removal of fluid material to at least one relief set of air cells that includes at least two contiguous air cells among the plurality of air cells spread across at least one of the plurality of linear rows and the plurality of longitudinal columns.

* * * * *